(12) United States Patent
Martin

(10) Patent No.: US 8,916,093 B2
(45) Date of Patent: Dec. 23, 2014

(54) METHOD AND APPARATUS FOR DECONTAMINATING ENCLOSED SPACES

(75) Inventor: Anthony M. Martin, Andover (GB)

(73) Assignee: Bioquell UK Limited, Andover, Hampshire (GB)

( * ) Notice: Subject to any disclaimer, the term of this patent is extended or adjusted under 35 U.S.C. 154(b) by 771 days.

(21) Appl. No.: 12/598,812

(22) PCT Filed: May 29, 2008

(86) PCT No.: PCT/GB2008/001811
§ 371 (c)(1),
(2), (4) Date: Nov. 4, 2009

(87) PCT Pub. No.: WO2008/145990
PCT Pub. Date: Dec. 4, 2008

(65) Prior Publication Data
US 2010/0143189 A1 Jun. 10, 2010

(30) Foreign Application Priority Data
May 30, 2007 (GB) .................................. 0710331.0

(51) Int. Cl.
*A61L 2/20* (2006.01)
(52) U.S. Cl.
CPC ............. *A61L 2/208* (2013.01); *A61L 2202/25* (2013.01)
USPC ................ 422/28; 422/30; 422/292; 422/305
(58) Field of Classification Search
CPC ........................... A61L 2/208; A61L 2202/25
USPC ...................... 422/28, 30, 124, 292, 298, 305
See application file for complete search history.

(56) References Cited

U.S. PATENT DOCUMENTS

| 2,662,332 A | 12/1953 | McIntire |
| 3,770,203 A | 11/1973 | Dyar |

(Continued)

FOREIGN PATENT DOCUMENTS

| CH | 689 178 | 11/1998 |
| EP | 1 655 041 A1 | 5/2006 |

(Continued)

OTHER PUBLICATIONS

Bioquell, The Clams C—multi function hydrogen peroxide vapor generator, http://www.bioquell.com/us/default.asp?Ctr1=1&ex526=1&pid=526&id=526, design published at least as early as Jan. 17, 2008.

(Continued)

*Primary Examiner* — Timothy Cleveland
(74) *Attorney, Agent, or Firm* — Workman Nydegger

(57) ABSTRACT

The disclosure relates to an apparatus (10) for decontaminating an enclosure that includes a passage having an inlet (18) to receive a carrier gas from the enclosure, an outlet (31) to discharge the carrier gas to the enclosure, a fan (21) for causing a low of carrier gas through the passage from the inlet to the outlet, and a vapour generator (19) where a decontaminant vapour is introduced into the flow of carrier gas to be discharged with the flow at the outlet to decontaminate the enclosed space. A further fan (33) delivers a separate flow of gas from the enclosure bypassing the passageway in which the decontaminant vapour is introduced to be delivered into the enclosure from outlet vents (32) adjacent the vapour outlets (31) to assist in dispersing the carrier gas containing decontaminant vapour throughout the enclosure.

13 Claims, 7 Drawing Sheets

(56) References Cited

U.S. PATENT DOCUMENTS

Figure 1:
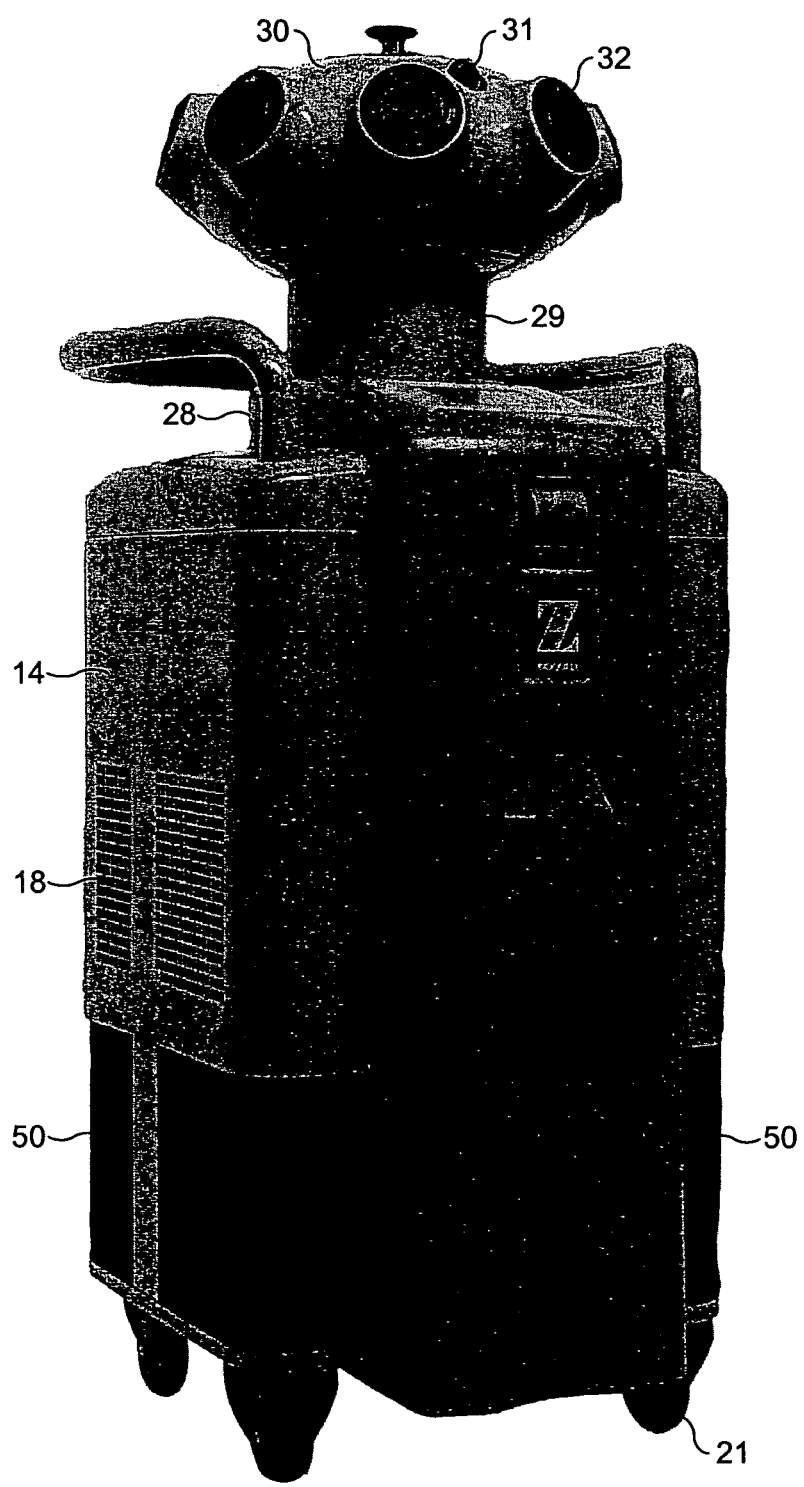

| | | | |
|---|---|---|---|
| 4,244,712 A | 1/1981 | Tongret | |
| D276,841 S | 12/1984 | Church | |
| 4,863,688 A | 9/1989 | Schmidt et al. | |
| D325,252 S | 4/1992 | Morris et al. | |
| 5,173,258 A | 12/1992 | Childers | |
| D337,592 S | 7/1993 | Hider et al. | |
| D351,902 S | 10/1994 | Shaw | |
| D352,350 S | 11/1994 | Rambo et al. | |
| 5,480,615 A | 1/1996 | Curry | |
| D386,255 S | 11/1997 | Ying-teng | |
| 5,825,975 A | 10/1998 | Privas | |
| 5,906,794 A | 5/1999 | Childers | |
| D419,230 S | 1/2000 | Ciccone | |
| 6,096,265 A | 8/2000 | Mezger et al. | |
| D435,096 S | 12/2000 | Meeks et al. | |
| D445,116 S | 7/2001 | Evans et al. | |
| 6,455,075 B1 | 9/2002 | Larose | |
| 6,589,479 B2 | 7/2003 | Dufresne et al. | |
| 6,630,105 B1 | 10/2003 | O'Neill et al. | |
| 6,840,744 B2 | 1/2005 | Watling | |
| 6,887,710 B2 | 5/2005 | Call et al. | |
| D508,735 S | 8/2005 | Klein | |
| 7,014,813 B1 | 3/2006 | Watling | |
| D519,622 S | 4/2006 | Cocchi | |
| 7,025,932 B2 | 4/2006 | Martin et al. | |
| D521,620 S | 5/2006 | Tseng et al. | |
| 7,186,371 B1 | 3/2007 | Watling | |
| D572,356 S | 7/2008 | Harber | |
| D595,823 S | 7/2009 | Parr | |
| 2006/0008379 A1 | 1/2006 | Mielnik et al. | |
| 2007/0098592 A1* | 5/2007 | Buczynski et al. | 422/292 |
| 2008/0038166 A1* | 2/2008 | Hill et al. | 422/292 |
| 2008/0247922 A1 | 10/2008 | Adams et al. | |

FOREIGN PATENT DOCUMENTS

| | | |
|---|---|---|
| EP | 1 487 503 B1 | 9/2007 |
| GB | 2 354 443 | 3/2001 |
| GB | 2 360 454 | 9/2001 |
| JP | 54-050184 | 4/1979 |
| JP | 54-082893 | 7/1979 |
| JP | 61-234859 | 10/1986 |
| JP | 03-224469 | 10/1991 |
| JP | 08-266596 | 10/1996 |
| JP | 9-215741 | 8/1997 |
| JP | 63-011163 | 1/1998 |
| JP | 11-226106 | 8/1999 |
| JP | 2001-212431 | 8/2001 |
| RU | 2 054 295 | 2/1996 |
| WO | WO98/44958 | 10/1998 |
| WO | WO00/38746 | 7/2000 |
| WO | WO00/74734 | 12/2000 |
| WO | WO01/21223 | 3/2001 |
| WO | WO02/07788 | 1/2002 |
| WO | WO02/11774 | 2/2002 |
| WO | WO02/11864 | 2/2002 |
| WO | WO 03/082355 | 10/2003 |
| WO | WO 2006/031957 A1 | 3/2006 |

OTHER PUBLICATIONS

Bioquell, The Clams L Small Chamber Hydrogen Peroxide Vapor (HPV) Generator, http://www.bioquell.com/us/default.asp?Ctr1=1&ex526=1&pid=526&id=526, design published at least as early as Jan. 17, 2008.

David Watling et al., *Theoretical Analysis of the Condensation of Hydrogen Peroxide Gas and Water Vapour as Used in Surface Decontamination*, PDA Journal of Pharmaceutical Science and Technology, vol. 56, No. 6, Nov./Dec. 2002, pp. 291-299.

Seymour S. Block, Ph.D., *Disinfection, Sterilization, and Preservation*, 5$^{th}$ Edition, Lippincott Williams & Wilkins, Dec. 200, pp. 188-189.

* cited by examiner

METHOD AND APPARATUS FOR DECONTAMINATING ENCLOSED SPACES

BACKGROUND OF THE INVENTION

1. Field of the Invention

This invention relates to methods and apparatus used for the decontamination of enclosed spaces such as pharmaceutical clean rooms, isolators and hospital wards.

2. Present State of the Art

WO-A-2006/031957 discloses a flash vaporizer which provides a constant flow of vaporized hydrogen peroxide or other antimicrobial compounds for rapidly sterilizing large enclosures such as rooms or buildings. The vaporizer includes a heated block which defines an interior bore or bores. The flowpath created by the bore or bores increases in cross sectional area as the hydrogen peroxide passes through the block to accommodate the increase in volume during the conversion from liquid to gas. The vapor is injected into dry air in a duct that circulates it to the large enclosure.

US-A-2006/0008379 discloses a system for microbially and/or chemically decontaminating a room such as hotel room and includes a vapor generator which supplies a decontaminant vapor, such as hydrogen peroxide vapor to the room. The room is then aerated to a level at which it is safe for normal occupants to enter. By using a two step aeration, with a second step at lower humidity than the first, the concentration of residual hydrogen peroxide is reduced rapidly to safe levels of 1 ppm or less, typically about 0.5 ppm, in under four hours. The room is rendered substantially free of contaminants, such as those responsible for Severe Acute Respiratory Syndrome (SARS), Norwalk virus, and unpleasant odors.

EP-A-1655041 discloses a mobile decontamination vehicle comprising a vessel containing a supply of hydrogen peroxide; a catalytic reactor coupled to the vessel to receive a first flow of hydrogen peroxide and to at least partially decompose the hydrogen peroxide into decomposition products. A jet of said decomposition products is directed in the opposite direction to the required direction of travel of the vehicle to provide a thrust to propel the vehicle. A supply of undecomposed hydrogen peroxide is carried in the apparatus for'use at a location to be decontaminated.

Vapour phase bio-decontamination is generally a four phase process. During the first phase the relative humidity inside the chamber is brought to a pre-set value. This is followed by the second phase during which the active vapour concentration inside the chamber is raised to the required value. The next phase is to maintain the active vapour concentration inside the chamber for a sufficient period of time to ensure that bio-decontamination is achieved. The fourth and final phase is to remove the active vapour from the chamber generally by dilution with clean air.

The most commonly used vapour for bio-decontamination is hydrogen peroxide which is generated by "flash" evaporating an aqueous solution of about 30 to 35% w/v. The usual technique for producing the "flash" evaporated vapour is to drop the aqueous solution onto a heated plate held at a temperature above the boiling point of the liquid thus generating a vapour with the same weight ratio as the source liquid. There are two theories as to the action of the hydrogen peroxide; the earlier thinking was that the vapour should be maintained at a concentration below the dew point thus avoiding condensation, the other theory suggests that condensation is necessary to give a rapid bio-decontamination.

There are numerous patents covering the use of gaseous and vapour phase decontamination of enclosed spaces the most important of which are U.S. Pat. No. 5,173,258 and U.S. Pat. No. 7,014,813 B1.

U.S. Pat. No. 5,173,258 describes a single loop closed system in which the carrier gas is circulated from the vapour generator to the chamber to be bio-decontaminated and then back to the vapour generator. On returning to the vapour generator the carrier gas and vapours pass through a device to remove the active vapour and the water vapour thus allowing more hydrogen peroxide to be evaporated into the circulating carrier gas.

U.S. Pat. No. 7,014,813 describes a similar process but has a bypass loop inside the vapour generator. Thus the vapours are not removed from the circulating carrier gas on returning to the vapour generator during the second and third phases of the cycle. This allows a more rapid build up of vapour concentrations and is normally used in cycles when condensation is required.

In both types of bio-decontamination cycles (in which condensation is to be avoided or encouraged respectively) it is essential that the active vapours are distributed evenly throughout the chamber. In some systems the vapours are delivered from rotating nozzles at a velocity up to 20 m/sec and in others external fans are used to move the vapour mixture around the chamber. EP-A-1487503 discloses a portable apparatus for decontaminating an enclosed room or other space comprising a passageway having an air inlet at one end, an outlet at the other end and a pump to cause flow of air through the passageway from the inlet to the outlet. A heater heats the air flowing through the passageway to a predetermined temperature and a flash evaporator is in communication with the passageway. Liquid decontaminant is pumped from a supply of decontaminant to the evaporator to be evaporated and for the evaporant to be delivered to the air flow in the passage to flow in the air flow from the outlet to the rooms to be decontaminated. A universally rotating nozzle is provided at the outlet to distribute the decontaminant containing air throughout the enclosure.

The difficulty in achieving good vapour distribution arises because the air flow through the "flash" evaporator is limited firstly by the size of the evaporator and also because the carrier gas must be heated in order to avoid condensation in the delivery system. The use of rotating nozzles that produce high velocity streams of vapours is of limited value because the mass flow is small and hence the velocity of the plume will rapidly fall as it moves from the source. The addition of fans at different positions in the room is not ideal as their position may be critical to the success of the process and they add complexity to the set-up and management of the equipment.

The final stage of the bio-decontamination cycle is aeration in which the hydrogen peroxide is reduced to a safe level; two techniques in general use for the removal of the hydrogen peroxide from the chamber. The most common is to circulate the carrier gas containing the hydrogen peroxide through a catalyst bed reducing the hydrogen peroxide to water vapour and oxygen, two harmless chemicals. The carrier gas emerging from the catalyst is also commonly dried to remove the water vapour. This purified carrier gas is then returned to the chamber where the hydrogen peroxide concentration is reduced by dilution. The flow rate through the catalyst will determine the time necessary to reduce the hydrogen peroxide to an acceptable value. The vapour generator's catalyst and dryer will have a limited flow for the reasons given above and hence the time required to remove the hydrogen peroxide is likely to be long this is sometimes overcome by having a separate unit to remove the hydrogen peroxide and water vapour. In some rooms fitted with air conditioning systems it is possible to use the air supply and extract to supply fresh air to the room and hence speed up the aeration process.

SUMMARY OF THE INVENTION

The present invention addresses these two problems of vapour distribution and increased air flow during the aeration phase of the cycle while at the same time providing a single portable unit that may be used either on its own or daisy chained to a number of similar units for larger volume. chambers.

This invention provides a method of decontaminating an enclosure using an apparatus for generating within the enclosure a first flow of a carrier gas, introducing a decontaminant vapour into the first gas flow at a vapour generating station within the apparatus and circulating the first flow of carrier gas/decontaminant vapour from the apparatus to the enclosure, wherein a separate second flow of carrier gas is generated within the apparatus which is circulated with the first flow to the enclosure to assist the dispersal of the decontaminant vapour in the enclosure; wherein the first and second flows of carrier gas are separately discharged into the enclosure.

Preferably the second flow of carrier gas is greater than the first flow. More specifically it is preferred that the second flow of carrier gas is a plurality of times greater than the first flow.

The first and second flows may be merged downstream of where they discharge into the enclosure.

In the latter case the first and second flows may be coaxial where they discharge into the enclosure.

In any of the above methods the first and second flows of carrier gas may each have a plurality of separate discharges into the enclosure.

In the latter case the discharge of the first and second carrier gases may be equi-spaced around an axis and are directed outwardly of the axis to discharge into the enclosure.

Also in any of the above methods both first and second gas flows draw gas from the enclosure and discharge to the enclosure.

According to a further feature of the invention, following decontamination of the enclosed space, gas from the enclosure is circulated through a decomposition station in which the decontaminant carried by the gas is decomposed for disposal.

In the latter case the decomposition station may comprise a filter through which the vapour containing gas is drawn to decompose the decontaminant vapour for disposal.

The invention also provides an apparatus for decontaminating an enclosure comprising a passage having an inlet to receive a carrier gas from the enclosure, an outlet to discharge the carrier gas to the enclosure, fan means for causing a flow of carrier gas through the passage from the inlet to the outlet and a station in the passage where a decontaminant vapour is introduced into the flow of carrier gas to be discharged with the flow at the outlet to decontaminate the enclosed space, and means are provided for generating a separate flow of gas from the enclosure bypassing the passageway in which said decontaminant vapour is introduced and means are provided for discharging the two flows separately into the enclosure to assist in dispersing the carrier gas containing decontaminant vapour throughout the enclosure.

For example the means for generating the separate flow of gas may comprise further fan means.

Figure 3:
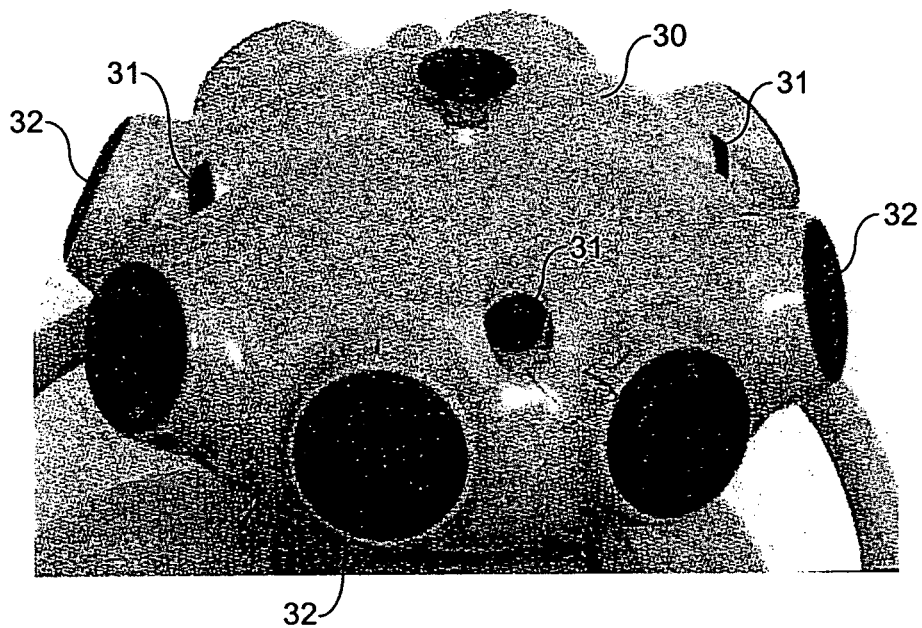

In one specific arrangement according to the invention a first set of radially facing nozzles are spaced apart around an axis through a duct connected to the station where decontaminant is added to receive carrier gas and decontaminant vapour and a second set of radially facing nozzles is connected to the means for producing the separate flow of carrier gas to deliver the carrier gas with the carrier gas/vapour to the enclosed space.

BRIEF DESCRIPTION OF THE DRAWINGS

The following is a description of some specific embodiments of the invention, reference being made to the accompanying drawings, in which:

FIG. 1 is a perspective view of a mobile decontamination apparatus for enclosed spaces such as hospital wards and pharmaceutical clean rooms;

FIG. 2 is a diagrammatic view of the apparatus illustrating the internal components;

FIGS. 3 and 4 show alternative arrangements of outlet nozzles for the apparatus of FIG. 1;

FIG. 5 shows an arrangement of multiple decontamination apparatus linked together with a common control system;

FIGS. 6 and 7 are views of modified forms of the apparatus of FIGS. 1 and 2 showing further arrangements of outlet nozzle; and FIG. 8 is a similar view to that of FIG. 6 with the control panel detached.

DETAILED DESCRIPTION OF THE PREFERRED EMBODIMENTS

Referring firstly to FIGS. 1 to 3 of the drawings, there is shown a combined gas generator and removal apparatus indicated generally at 10. The apparatus comprises a chassis 11 mounted on castor wheels 12 supported on swivel mountings 13 for ease of mobility of the apparatus around the room or enclosure.

The chassis of the apparatus is generally square and carries a main casing 14 also generally square in plan view and of generally upright form. The casing is divided by a transverse internal partition wall 15 into upper and lower housings 16 and 17 for vapour generation and vapour decomposition respectively.

The casing 14 around the upper housing 16 is formed with pairs of air inlet grilles 18 on opposite sides of the casing to allow air entry into the upper part of the casing. A hydrogen peroxide vapour generator 20 is mounted generally centrally in the upper part of the upper housing 16. The generator may be of the type described and illustrated in our WO-A-03/082355. The vapour generator has an air inlet at its lower end to which an outlet of a motor driven centrifugal fan 21 is coupled. The fan has an air inlet 22 in the air space in the lower part of the main cavity 16 which the air inlet grilles 18 open into. Air flow into the generator is heated by a band heater unit 19 in the lower part of the generator.

The vapour generator 20 has a supply tank 23 for aqueous hydrogen peroxide/solution having a feed conduit 24 connected to the generator. The conduit 24 has a motor driven metering pump 25 for delivering hydrogen peroxide/water to a flash evaporator unit 20 in the generator where the hydrogen peroxide is flash evaporated into a pre-heated air flow through the generator created by the fan 21.

The upper end of the vapour generator 20 has a distribution manifold 26 to which four outlet conduits 27 are connected.

The top of the casing has an annular collar 28 in which an upstanding neck 29 is fitted having a generally ellipsoidal shaped head 30 at its upper end. The conduits 27 extend upwardly from the manifold through the neck and collar into the head 30 where they are coupled to four radially outwardly facing nozzles 31 for discharging hydrogen peroxide vapour created the vapour generator 20 into the room or enclosure in which the apparatus is located. As best seen in FIG. 3, the nozzles 31 are equi-spaced around the upper side of the head 30.

The head 30 also has a number of air outlet vents 32 equi-spaced around the head. In the embodiment shown there are eight vents and it will be noted that the vents are substantially greater in aperture than the vapour nozzles 31. The air outlet vents are connected to outlets of a high throughput motor driven radial fan 33 positioned in the head within the nozzles and which draw air from the cavity within the head which is in direct communication with the upper cavity 16 of the main casing. Thus air is drawn from the inlet grilles 18 by the fan 33 and is discharged through the air outlet vents adjacent to the streams of hydrogen peroxide vapour discharged through the nozzles 31 to assist in distributing the hydrogen peroxide vapour throughout the room or enclosure in which the apparatus is mounted as described later.

The internal transverse partition wall 15 which divides the casing into upper and lower chambers is formed with a deep central well 40 in which a motor driven fan 41 is mounted communicating with the lower cavity 17 through an opening at the bottom of the well.

An inverted pyramidal housing 42 is mounted on the underside of the partition 15 over the well and has an inlet in which there is a motor driven fan 43. Within the housing there are flap valves 44 pivoted at the apex of the housing to control air flow into the housing 42.

The lower cavity 17 has inlets on either side of the cavity in which activated carbon beds 50 are mounted with H.E.P.A. filters 51 behind the beds. The activated carbon tends to shed "dust" which is caught by the filters.

The decontamination cycle comprises a first phase in which the evaporator and nozzle fans 21 and 33 are switched on together with the evaporator heater 20. This allows the whole generator and if necessary, the room/enclosure to be decontaminated to be brought to a stable temperature. Once thermal stability has been achieved the generator moves to a second phase of the decontamination cycle during which the hydrogen peroxide liquid pump 25 is switched on and hydrogen peroxide solution is "flash" evaporated and delivered at pressure to the distribution nozzles 31 where it exits and is mixed with the bulk air streams exiting the nozzles 32.

Figure 2:
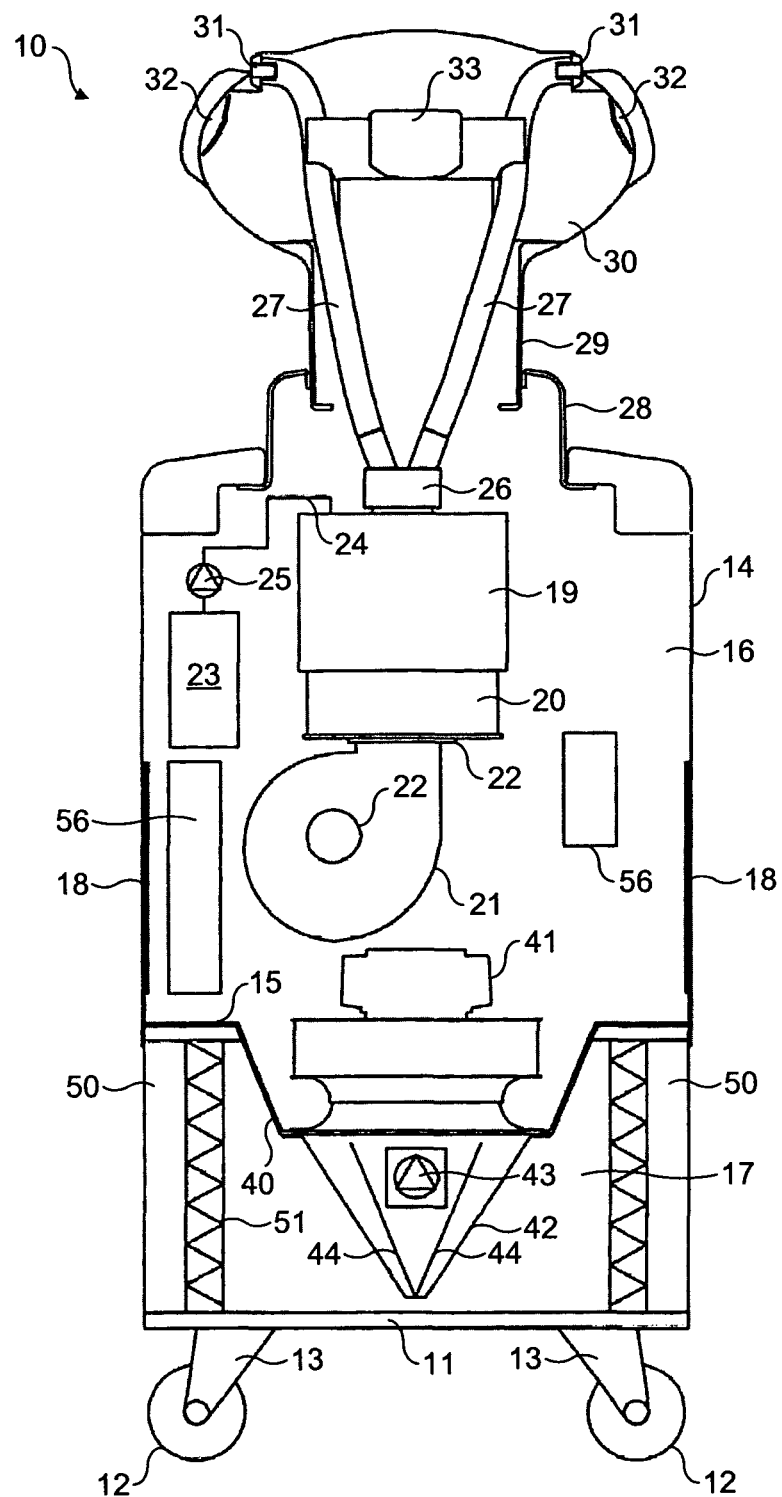

In the arrangement shown in FIGS. 1 and 2 the hydrogen peroxide vapour is delivered to the distribution nozzles 31 and the hydrogen peroxide and distribution air from fan 33 mix just outside the distribution nozzle although mixing could also take place within the nozzles 32 as described later.

It should be noted that during the first two phases of the decontamination cycle the air is drawn into the casing 14 through the inlets 18 and that the aeration fan 43 remains switched off. However, fan 43 is run during the gassing phase of the cycle to draw air from the upper housing 16 into the cavity 17 to decontaminate the spaces between the filters 50,51 and the fan 41 as the hydrogen peroxide vapour concentration in the surrounding atmosphere is increased during the gassing phase. This ensures that all of the internal spaces within the case 14 are decontaminated. The flap valves 44 stop unwanted air circulation during the gassing phase of the cycle from passing through the filters 50,51 and thus into the casing chamber 16.

Once the room or enclosure has been decontaminated the generator moves to the aeration phase of the cycle. In the arrangement disclosed in our European Patent Publication No. 1487503 referred to above a separate aeration unit is provided such as that disclosed in our EP-A-1305105. In accordance with a preferred feature of the present arrangement an aeration system is incorporated in the decontamination unit as will now be described.

In the aeration phase the hydrogen peroxide liquid pump 25 is switched off as is the evaporator heater 19. The fan 43 is also switched off but fan 41 is started. The operation of fan 41 opens the flap valves 44 and draws large quantities of air through the filters 50,51 which decompose the hydrogen peroxide to water and oxygen and at the same time absorb the water vapour. The fan 21 is left running together with fan 33 helping to cool down the evaporator but also to ensure good distribution of the air during aeration. The fan 41 will generally have a much greater capacity than the combined capacity of fans 21 and 33 and hence air will pass out of the case through the filters 18 as well as the nozzles 32. This high air flow generated by fan 41 will reduce the time taken for aeration. Once the hydrogen peroxide vapour concentration within the space to be decontaminated has reached a safe level the generator is switched off.

The whole of the cycle is controlled from outside of the area to be decontaminated using a computer connected to the equipment via a single cable. Placed inside the case 14 is electrical panel 55 with all of the necessary components and a further sensors unit 56 housing the necessary instruments.

Figure 4:
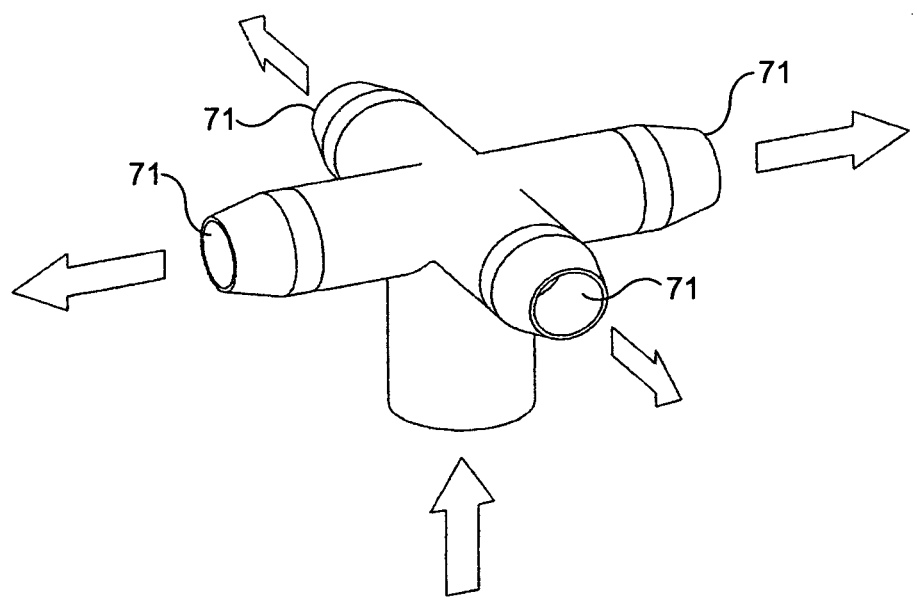

Two further nozzle/vent configurations are shown in FIGS. 3 and 4. FIG. 3 shows an arrangement of 8 outlet vents 32 equi-spaced from one another and facing radially outwardly. Four nozzles 31 for sterilant vapour are provided facing radially outwardly between alternate pairs of air outlet vents 32 while that in FIG. 4 has four air outlet vents 71 and the sterilant outlet nozzles are located within the air outlet vents. The effectiveness of the nozzles depends not only on their number but also on the quantity of air delivered from each outlet because the distance that the air vapour mixture will travel depends not only on the velocity at the outlet but also on the mass leaving each outlet.

Figure 5:
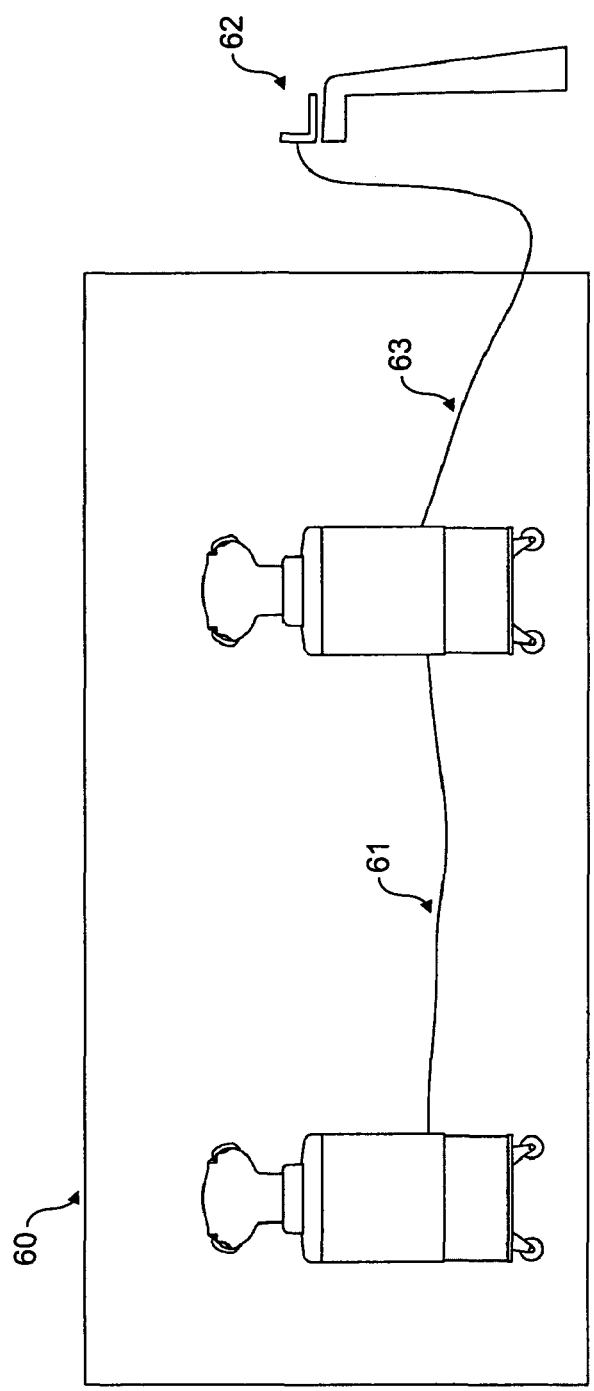

FIG. 5 shows a room 60 in which are placed two decontamination units connected by a control cable 61. Outside the room is a computer 62 connected to one of the decontamination units by a cable 63. The decontamination procedure is controlled from the computer placed outside of the room with all of the necessary data being fed through the cables 61 and 63. Each decontamination unit will have a limited evaporation capacity which will determine the maximum size of room that it can decontaminate in a sensible period of time, by daisy chaining additional decontamination units together there is no limit to the size of room that may be treated.

Figure 6:
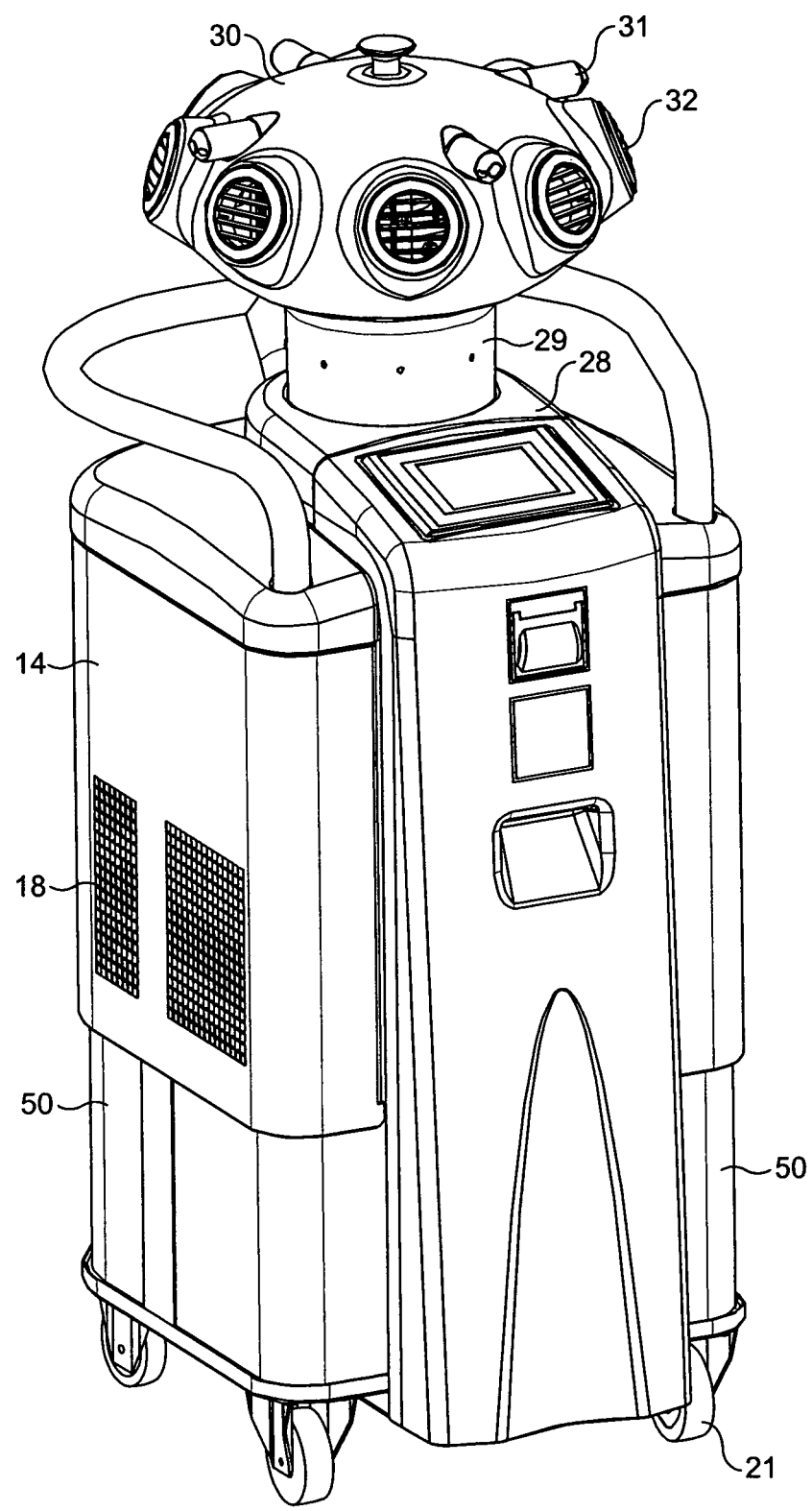

FIG. 6 of the drawings shows a further modified arrangement in which the vapour outlet nozzles 31 are extended to project between the air vents 32.

Figure 7:
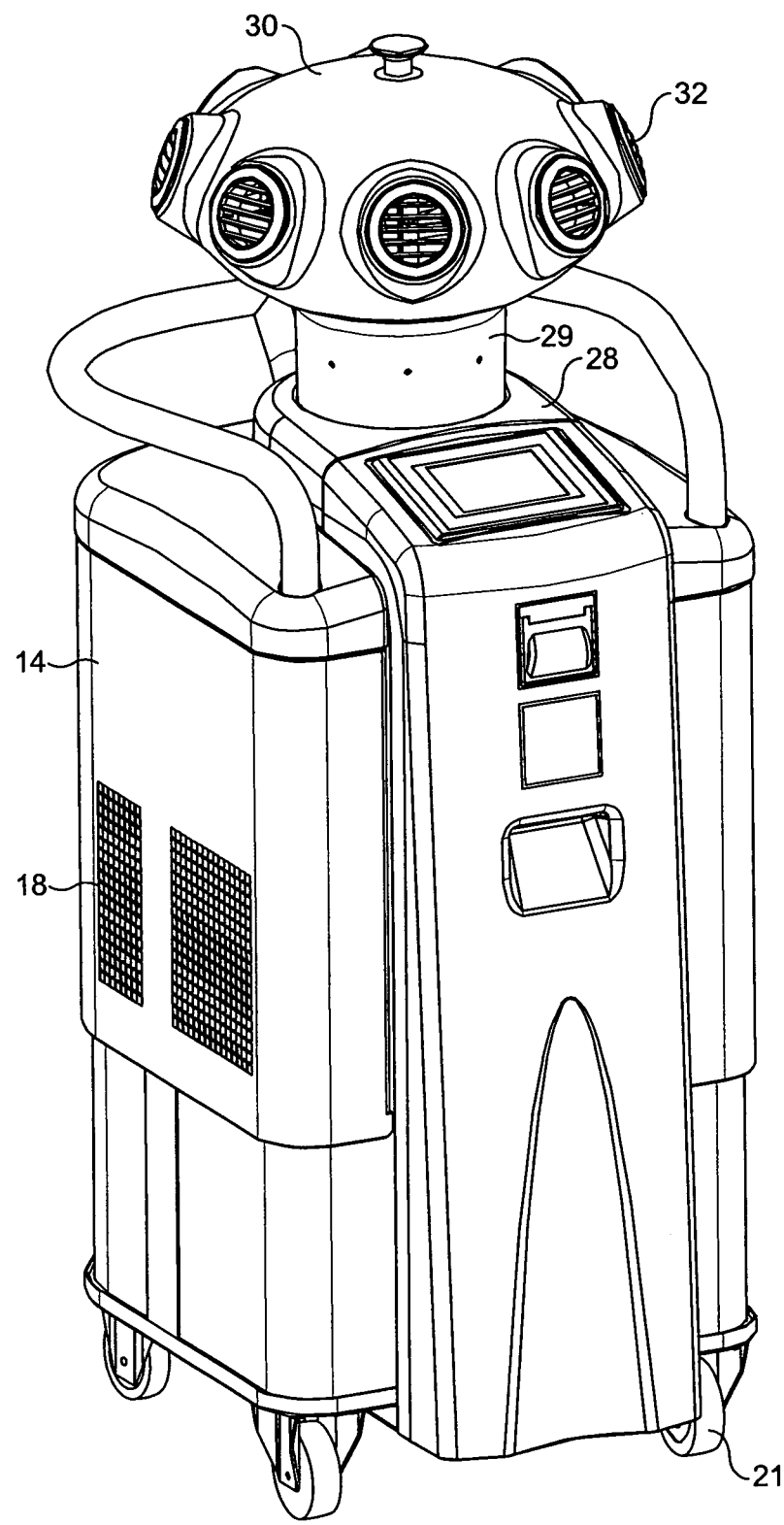

FIG. 7 shows an arrangement in which the vapour nozzles 31 are positioned concentrically within the air nozzles and so cannot be seen from outside the apparatus.

Figure 8:
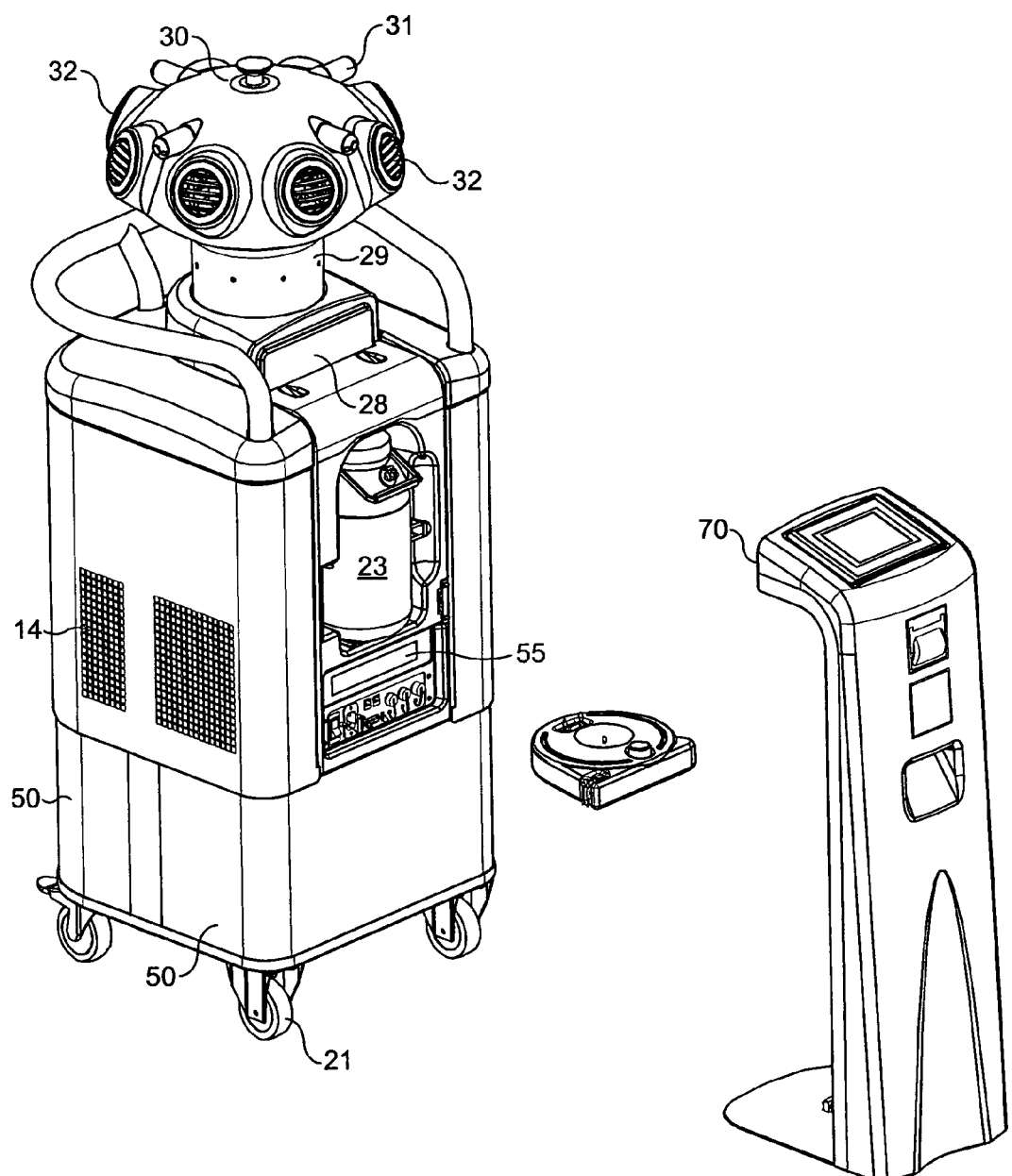

FIG. 8 shows the apparatus of FIG. 6 with the control module 70 detached revealing the sterilant container 23 and control unit 55 for the apparatus.

The invention claimed is:
1. A method of decontaminating an enclosure, comprising the steps of:
    placing a decontamination unit having a housing within the enclosure;
    operating the decontamination unit that is placed within the enclosure from a position outside the enclosure, the decontamination unit:
        generating a first flow of a carrier gas by drawing air into the decontamination unit;

introducing a decontaminant vapour into the first flow of the carrier gas at a vapour generating station within the decontamination unit;

circulating the first flow of carrier gas/decontaminant vapour from the decontamination unit around the enclosure;

generating a separate, second flow of carrier gas from within the decontamination unit by drawing air into the decontamination unit, the second flow being a plurality of times greater than the first flow; and circulating the second flow with the first flow around the enclosure to assist the dispersal of the decontaminant vapour in the enclosure, wherein the first and second flows of carrier gas are separately discharged from the decontamination unit into the enclosure and the second flow of carrier gas is passed through the decontamination unit without actively treating the second flow of carrier gas to modify the humidity thereof.

2. A method as claimed in claim 1, wherein the first and second flows merge downstream of where they discharge into the enclosure.

3. A method as claimed in claim 2, wherein the first and second flows are coaxial where they discharge into the enclosure.

4. A method as claimed in claim 1, wherein the first and second flows of carrier gas are each discharged into the enclosure through a plurality of separate openings to provide separate discharges.

5. A method as claimed in claim 4, wherein the plurality of separate openings are equi-spaced around an axis and are directed outwardly of the axis to discharge into the enclosure.

6. A method as claimed in claim 1, wherein both first and second gas flows draw gas from the enclosure and discharge to the enclosure without passing outside of the enclosure.

7. A method as claimed in claim 1, wherein, following decontamination of the enclosed space, gas from the enclosure is circulated through a decomposition station in which the decontaminant carried by the gas is decomposed for disposal.

8. A method as claimed in claim 7, wherein the decomposition station comprises a filter through which the vapour containing gas is drawn to decompose the decontaminant vapour for disposal.

9. The method as recited in claim 1, further comprising:

wherein the step of circulating the first flow of carrier gas/decontaminant vapour comprises discharging the first flow of carrier gas/decontaminant vapour from the decontamination unit and into the enclosure by passing the first flow of carrier gas/decontaminant vapour out through a plurality of nozzles that are disposed on and are radially spaced apart around the housing; and wherein the step of circulating the second flow with the first flow comprises discharging the second flow of carrier gas from the decontamination unit and into the enclosure by passing the second flow of carrier gas out through a plurality of outlets vents that are disposed on and are radially spaced apart around the housing, the outlet vents being located adjacent to or co-axial with the nozzles so that the second flow of the carrier gas assists in dispersing the first flow of carrier gas/decontaminant vapour in the enclosure.

10. A method as claimed in claim 1, wherein the first flow of carrier gas and the second flow of carrier gas are both drawn into the housing through a common first inlet formed on the housing.

11. A method as claimed in claim 1, further comprising:

generating the first flow of the carrier gas by using a first fan located within the housing to draw air from the enclosure into the housing; and generating the second flow of the carrier gas by using a second fan located within the housing to draw air from the enclosure into the housing.

12. A method as claimed in claim 11, wherein the housing has an encircling sidewall that bounds a compartment, the first fan, second fan, and vapour generating station being disposed within the compartment.

13. A method as claimed in claim 11, further comprising generating a third flow of a carrier gas by using a third fan to draw air from the enclosure into the housing, the third flow of carrier gas passing through a decomposition station disposed on or within the housing, the decontamination station decomposing the decontaminant vapour carried in the third flow.

* * * * *